United States Patent
Warren

(10) Patent No.: US 11,289,888 B2
(45) Date of Patent: Mar. 29, 2022

(54) SEAL APPARATUS AND METHOD OF USING THE SAME

(71) Applicant: Thomas L. Warren, West Hampton, MA (US)

(72) Inventor: Thomas L. Warren, West Hampton, MA (US)

(73) Assignee: John A. Morin, Easthampton, MA (US)

( * ) Notice: Subject to any disclaimer, the term of this patent is extended or adjusted under 35 U.S.C. 154(b) by 0 days.

(21) Appl. No.: 16/382,572

(22) Filed: Apr. 12, 2019

(65) Prior Publication Data

US 2019/0316679 A1    Oct. 17, 2019

Related U.S. Application Data

(60) Provisional application No. 62/657,768, filed on Apr. 14, 2018.

(51) Int. Cl.
| | | |
|---|---|---|
| *H02G 3/22* | (2006.01) | |
| *F16J 15/02* | (2006.01) | |
| *F16L 5/10* | (2006.01) | |
| *F16J 15/06* | (2006.01) | |

(52) U.S. Cl.
CPC .............. *H02G 3/22* (2013.01); *F16J 15/022* (2013.01); *F16L 5/10* (2013.01); *F16J 15/061* (2013.01)

(58) Field of Classification Search
CPC ...... B60R 16/0222; H02G 3/088; H02G 3/22; F16L 5/10; Y10T 16/063; F16J 15/022
See application file for complete search history.

(56) References Cited

U.S. PATENT DOCUMENTS

| | | | | | |
|---|---|---|---|---|---|
| 2,115,495 | A | * | 4/1938 | Mapelsden | H02G 3/083 174/70 R |
| 2,225,472 | A | * | 12/1940 | Franklin | H02G 3/083 277/604 |
| 2,668,316 | A | * | 2/1954 | Sturtevant | B62D 25/14 16/2.2 |
| 3,243,206 | A | * | 3/1966 | Samer | F16L 5/027 285/154.1 |
| 3,768,115 | A | * | 10/1973 | Hoffmann | F16C 11/04 16/2.1 |
| 4,383,692 | A | * | 5/1983 | Proctor | F16L 5/027 277/606 |
| 5,056,801 | A | * | 10/1991 | Beadle | B60S 1/34 277/577 |
| 5,071,143 | A | * | 12/1991 | Byerly | F16L 5/025 174/152 G |
| D360,820 | S | * | 8/1995 | Haase | D8/356 |
| 5,693,910 | A | * | 12/1997 | Gretz | H02G 3/083 174/153 G |
| 5,739,475 | A | * | 4/1998 | Fujisawa | B60R 16/0222 174/153 G |

(Continued)

*Primary Examiner* — Nicholas L Foster

(74) *Attorney, Agent, or Firm* — McCarter & English, LLP

(57) ABSTRACT

Exemplary embodiments are directed to a seal apparatus for sealing an opening of a structure having a thickness at the opening. The seal apparatus includes a first section disposed at a proximal end, a second section disposed at a distal end, and an intermediate section disposed between the first and second sections. The first section defines a cone-like configuration. An opening extends through the first section, the second section, and the intermediate section.

19 Claims, 14 Drawing Sheets

(56) References Cited

U.S. PATENT DOCUMENTS

| | | | | |
|---|---|---|---|---|
| 6,058,562 | A * | 5/2000 | Satou | B60R 16/0222 16/2.1 |
| 6,572,070 | B2 * | 6/2003 | Arciero | B60K 13/04 248/60 |
| 6,825,416 | B2 * | 11/2004 | Okuhara | B60R 16/0222 174/151 |
| RE38,788 | E * | 9/2005 | Satou | F16L 5/10 16/2.1 |
| 9,755,412 | B2 * | 9/2017 | Wang | H02G 3/22 |
| 2004/0206538 | A1 * | 10/2004 | Okuhara | B60R 16/0222 174/650 |
| 2017/0148551 | A1 * | 5/2017 | Gakuhari | H02G 3/085 |

* cited by examiner

SEAL APPARATUS AND METHOD OF USING THE SAME

CROSS-REFERENCE TO RELATED APPLICATIONS

This application claims the benefit of U.S. Provisional Patent Application No. 62/657,768, which was filed on Apr. 14, 2018. The entire content of the foregoing provisional patent application is incorporated herein by reference.

BACKGROUND

Various medical and scientific processes require the transfer of medicine, gases or chemicals into and/or out of a vessel while creating a sterile, liquid and air tight seal through a removable or permanent entry device. Traditional seal assemblies include nuts, washers, and/or quick connect features that can result in leaks between one or more components, and can increase the cost of assembly due to the number of components needed.

SUMMARY

In accordance with embodiments of the present disclosure, an exemplary seal apparatus for sealing an opening of a structure having a thickness at the opening is provided. The seal apparatus includes a first section, a second section, and an intermediate section. The first section is disposed at a proximal end of the seal apparatus. In one embodiment, the first section defines a cone-like configuration. The second section is disposed at a distal end of the seal apparatus. The intermediate section is disposed between the first and second sections. An opening extends through the first section, the second section, and the intermediate section.

The opening extending through the first section, the second section, and the intermediate section can be configured to receive therethrough a flexible conduit. In some embodiments, a plurality of relief areas can be formed in the first section. The relief areas can extend a partial distance into a thickness of the first section and enable the first section to compress or collapse under pressure during passage of the first portion through the opening of the structure. A diameter of the first section can be dimensioned greater than a diameter of the opening of the structure. The first section is configured to be temporarily compressed and/or collapsed during passage through the opening of the structure, and configured to expand to an original expanded configuration after passage through the opening of the structure. An inner wall of the first section forms a seal between the first section and the structure after expansion of the first section to the original expanded configuration.

In some embodiments, a diameter of the intermediate section can be dimensioned greater than a diameter of the opening of the structure. During assembly of the seal apparatus with the structure, the intermediate section can be compressed within the opening of the structure to create a seal between the intermediate section and the opening of the structure. In some embodiments, a length of the intermediate section can be dimensioned smaller than the thickness of the structure at the opening. In such embodiments, during assembly of the seal apparatus with the structure, inner walls of the first and second sections are configured to be compressed against opposing surfaces of the structure due to the dimensional difference between the length of the intermediate section and the thickness of the structure at the opening.

In some embodiments, the seal apparatus is configured to form a first seal between an inner wall of the first section and one wall of the structure, form a second seal between an inner wall of the second section and an opposing wall of the structure, and form a third seal between the intermediate section and an inner surface of the opening of the structure. In some embodiments, a relief groove can be formed in an inner wall of the second section.

In accordance with embodiments of the present disclosure, an exemplary system for sealing an opening of a structure having a thickness at the opening is provided. The system includes a first seal apparatus and a conduit. The first seal apparatus includes a first section disposed at a proximal end, a second section disposed at a distal end, and an intermediate section disposed between the first and second sections. The first section can define a cone-like configuration. An opening extends through the first section, the second section, and the intermediate section. The conduit is disposed within and extends through the opening of the first seal apparatus.

In some embodiments, the first seal apparatus is bonded to or capable of being bonded to the conduit. In some embodiments, a position of the first seal apparatus along the conduit is maintained via a friction fit. A connection between the first seal apparatus and the conduit forms a fluid-tight seal. In some embodiments, a second seal apparatus can be connected to the conduit and faces an opposing direction from the first seal apparatus.

In accordance with embodiments of the present disclosure, an exemplary method of sealing an opening of a structure having a thickness at the opening is provided. The method includes positioning a first section of a seal apparatus adjacent to the opening of the structure. The seal apparatus includes the first section disposed at a proximal end and defining a cone-like configuration, a second section disposed at a distal end, and an intermediate section disposed between the first and second sections. An opening extends through the first section, the second section, and the intermediate section. The method includes compressing the first section during passage of the first section through the opening of the structure. The method includes expanding the first section into an expanded configuration after passage of the first section through the opening of the structure. After passage of the first section through the opening of the structure, a first seal is formed between an inner wall of the first section and one wall of the structure, a second seal is formed between an inner wall of the second section and an opposing wall of the structure, and a third seal is formed between the intermediate section and an inner surface of the opening of the structure.

Embodiments of the present invention provide an overmolded seal apparatus that seals the interface between flexible conduits and openings, and methods of using the seal apparatus.

BRIEF DESCRIPTION OF THE DRAWINGS

The accompanying drawings, which are incorporated in and constitute a part of this specification, illustrate one or more embodiments of the invention and, together with the description, help to explain the invention. In the drawings.

DETAILED DESCRIPTION

Figure 1:
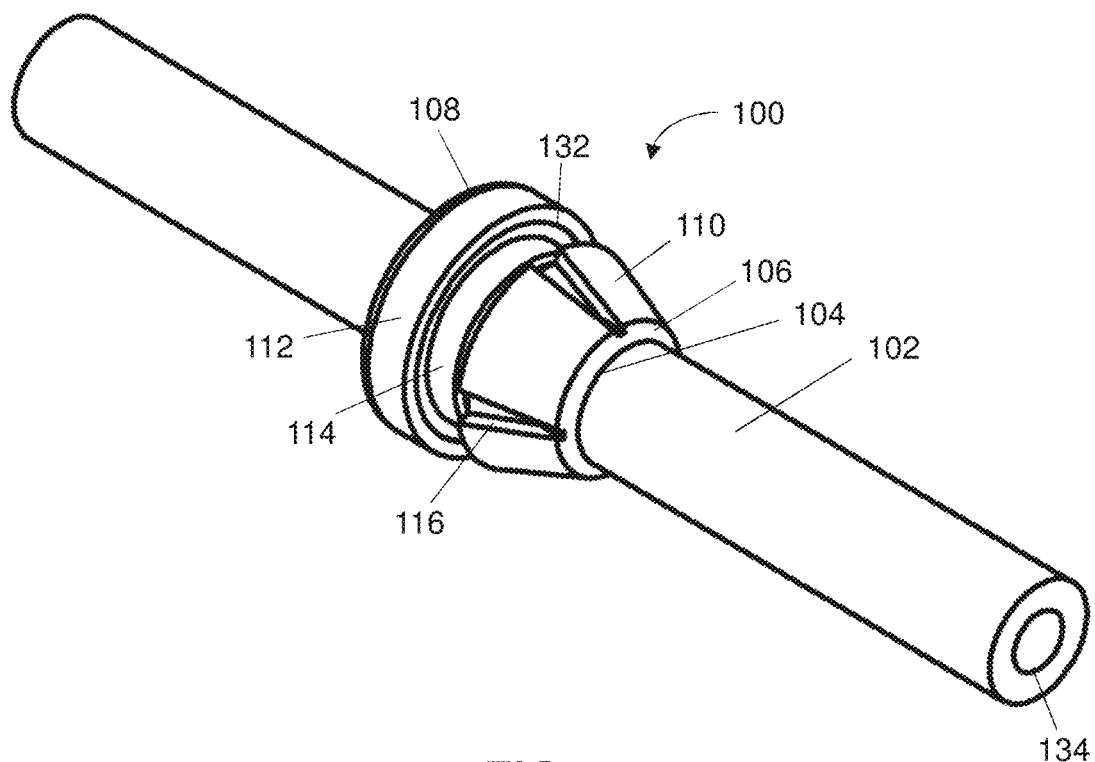
FIG. 1 is a diagrammatic, perspective view of a seal apparatus in an exemplary embodiment.
Figure 2:
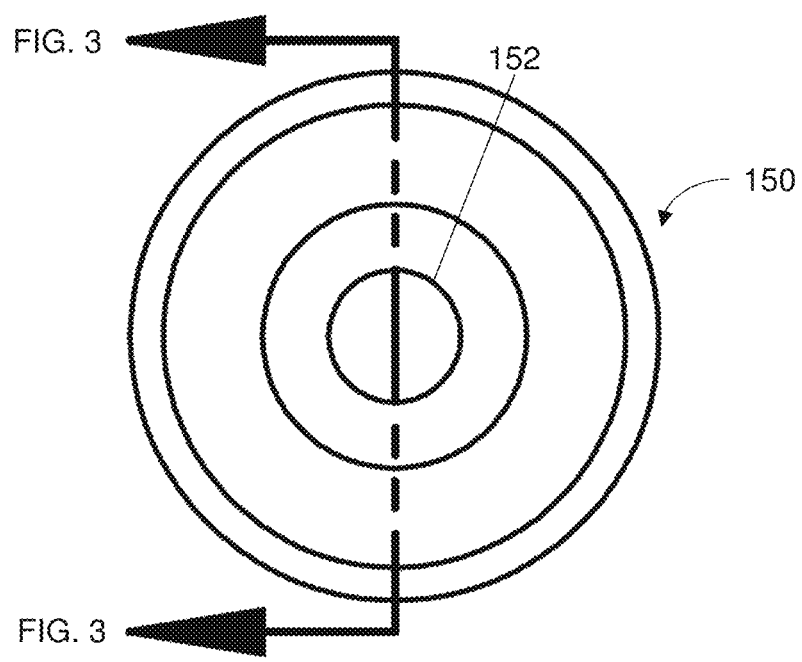
FIG. 2 is a diagrammatic, front view of a seal apparatus of FIG. 1 including a cap prior to assembly.

Embodiments provide a seal apparatus specifically designed for use with flexible conduits such as, but not limited to, silicone tubing. The seal apparatus can be used with a variety of entry devices including, but not limited to, a sanitary fitting, bottle caps, tanks, stoppers, pass-through clean room walls, or the like. In one embodiment the seal apparatus may be over molded onto the flexible conduit. The seal apparatus includes a top portion with a collapsible cone-like portion that forces the bottom section towards itself and creates a seal below the opening. This in part is accomplished by creating a space between the bottom section and the base of the cone section that is smaller than the thickness of the item the seal is to pass through. In addition, the intermediate section of the seal apparatus (e.g., the section between the top and bottom sections) intentionally has a diameter larger than the diameter of the opening which the seal apparatus passes through to also create a seal along the entire circumference of the interior surfaces of the opening. The seal apparatus may be made from a (LSR) Liquid Silicone Rubber such as BlueStar's LSR-60 Resin or similar material. Alternatively, in another embodiment, the seal apparatus may be provided as a single piece and then bonded to the flexible conduit such as by using a medical grade RTV silicon adhesive such as BlueStar's MED ADH 4100 RTV or similar types of adhesive to bond the single piece to silicone tubing.

FIGS. 1-4 are diagrammatic, perspective, front and cross-sectional views of a seal apparatus 100 in an exemplary embodiment. As an example, in FIGS. 2-3, the seal apparatus 100 is illustrated in combination with a cap 150 (e.g., cover, lid, or the like) prior to assembly. In one embodiment, the seal apparatus 100 can be over molded onto a flexible conduit 102, such as silicone tubing. In such an embodiment, the conduit 102 can be inserted into a central inner opening 104 of the seal apparatus 100, the position of the seal apparatus 100 can be selected along the length of the conduit 102, and adhesive, surface welding, and/or a friction fit can be used to create a seal between the seal apparatus 100 and the conduit 102. Although not applicable in a high pressure environment, in an alternate embodiment in which the seal apparatus 100 would be deployed in a lower or intermediate pressure environment, a friction fit could be used to maintain the position of the seal apparatus 100 at the desired location of the conduit 102. The conduit 102 can be used to transport or allow passage of fluid, gas, combinations thereof, or the like. The inner opening 104 extends along a central longitudinal axis 124 of the entire length of the seal apparatus 100 to accommodate the conduit 102. In one embodiment, the diameter of the opening 104 can be formed to be smaller than the outer diameter of the conduit 102 to create a friction fit and seal between the seal apparatus 100 and the conduit 102. In one embodiment, the seal apparatus 100 can be formed as a single unit with the conduit 102.

The seal apparatus 100 includes a proximal end 106 (e.g., a feed side, a top portion, or the like) and an opposing distal end 108 (e.g., an exit side, a bottom portion, or the like). The seal apparatus 100 includes a first section 110 defining a substantially triangular or cone-shaped configuration and extending from the proximal end 106 towards the distal end 108. The seal apparatus 100 includes a second section 112 extending from the distal end 108 towards the proximal end 106. The seal apparatus 100 includes an intermediate section 114 disposed between the first and second sections 110, 112 and defining a diameter dimensioned smaller than the diameter of the first and second sections 110, 112.

The first section 110 includes radially spaced grooves, cutouts or relief areas 116 extending a partial distance into the thickness of the first section 110. In one embodiment, the relief areas 116 extend from an external or outer surface down a partial distance into the first section 110. In one embodiment, the first section 110 includes relief areas 116 formed as cavities within the first section 110 without extending to the outer surface. In one embodiment, the relief areas 116 define a substantially triangular configuration (see, e.g., FIG. 1) having a point at or near the proximal end 106 and tapering outwardly towards an inner wall 118 of the first section 110. The inner wall 118 can extend substantially perpendicularly to the central longitudinal axis 124 of the seal apparatus 100. The relief areas 116 provide flexibility to the first section 110 such that during insertion of the first section 110 through an opening in a structure during assembly (e.g., into an opening 152 of the cap 150), the first section 110 can flex and/or collapse (e.g., in the direction of the distal end 108 and/or downward toward the opening 104) to allow the first section 110 to be pulled through the opening of the structure. The webbing left behind in the first section 110 between the relief areas 116 provides added strength to the structure of the seal apparatus 100, and forms a seal surface or area at the inner wall 118 of the first section 110.

The cone shape at the top of the seal apparatus 100 may include four relief areas 116 radially spaced from each other, but the size, shape and number of relief areas 116 cored into the seal apparatus 100 can be modified to fit into various styles of covers and/or vessels. In some embodiments, on a larger size conduit 102, the relief areas 116 may not be needed because the hollow area or inner passage 134 of the conduit 102 provides the area needed for the cone shape to collapse. For example, for conduit 102 having an inner passage 134 with a diameter dimensioned equal to or greater than about 0.625 inches, the relief areas 116 may be excluded from the seal apparatus 100. In some embodiments, the relief areas 116 can be included in the seal apparatus 100 for any size of the conduit 102 to assist in further flexing and collapsing of the seal apparatus 100 during installation.

In some embodiments, the inclusion of or the number of relief areas 116 can depend on the overall outer diameter of the seal apparatus 100. For example, if the seal apparatus 100 has an overall outer diameter equal to or below about 0.750 inches, the relief areas 116 can be included in the first section 110 to provide sufficient flexibility to the first section 110. As a further example, if the seal apparatus 100 has an overall outer diameter greater than about 0.751 inches, the first section 110 can be formed without relief areas 116 or with a smaller number of relief areas 116 due to the flexibility provided by the material itself.

Figure 4:
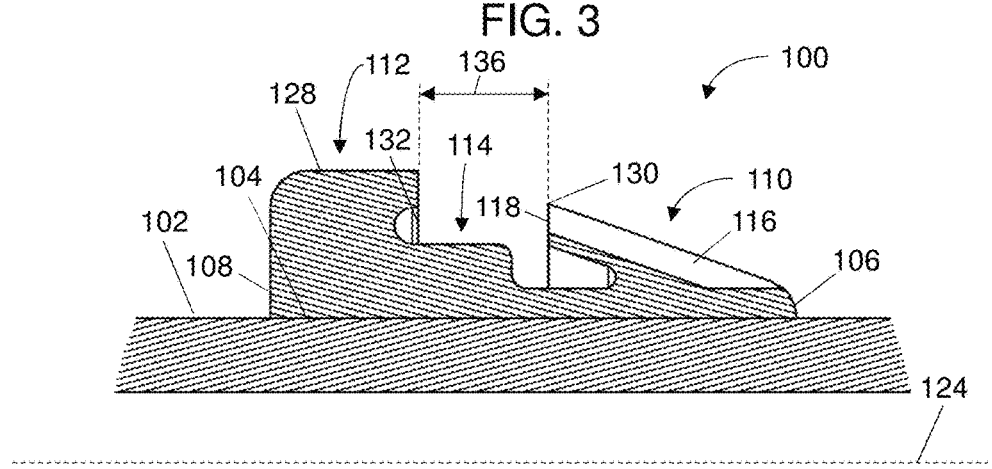
FIG. 4 is a diagrammatic, detailed cross-sectional view of a seal apparatus of FIG. 2.
Figure 4:
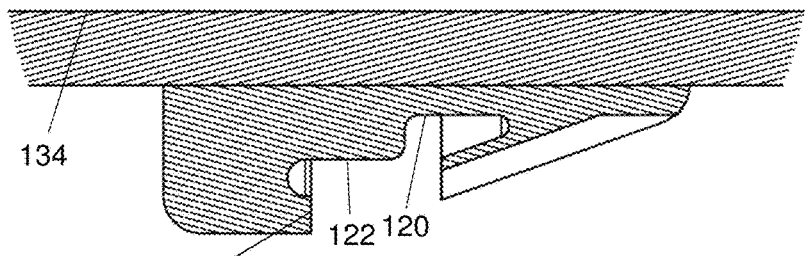

With specific reference to FIG. 4, the intermediate section 114 includes a proximal portion 120 and a distal portion 122 forming a step. The proximal and distal portions 120, 122 can extend substantially parallel to the central longitudinal axis 124. The proximal portion 120 can be disposed adjacent to the inner wall 118 of the first section 110, and defines a diameter dimensioned smaller than a diameter of the distal portion 122. The smaller diameter of the proximal portion 120 creates a radial groove or space immediately behind the proximal portion 120.

During assembly of the seal apparatus 100 with the cap 150, the radial groove or space formed by the proximal portion 120 provides room into which the first section 110 can extend during flexing and/or collapsing. The distal portion 122 includes a diameter dimensioned slightly greater than the diameter of the opening 152 of the cap 150 (or any structure to be assembled with the seal apparatus 100). The dimensional difference ensures that a friction seal is created between the intermediate section 114 and the inner surface of the opening 152 after assembly and engagement of the seal apparatus 100 with the cap 150. In some embodiments, the diameter of the intermediate section 114 can be, e.g., about 5% greater, about 6% greater, about 7% greater, about 5-6% greater, about 6-7% greater, about 5-7% greater, or the like, than the diameter of the opening 152 to create the sealing effect noted above.

Still with reference to FIG. 4, the second section 112 includes an inner wall 126 extending substantially perpendicularly to the central longitudinal axis 124. The inner wall 126 can face and oppose the inner wall 118 of the first section 110. The inner walls 118, 126 can extend substantially parallel to each other. The distance or length 136 of the intermediate section 114 as measured between the inner walls 118, 126 can be dictated by the thickness 158 of the item (e.g., cap 150) around which the seal is being employed. In some embodiments, the length 136 can be dimensioned less than the actual thickness 158 of the item such that after assembly of the seal apparatus 100 with the item, compressibility of the first and second sections 110, 112 on opposing sides of the item contributes to the sealing effect. In some embodiments, the length 136 can be, e.g., about 20% smaller, about 25% smaller, about 30% smaller, about 20-25% smaller, about 25-30% smaller, about 20-30% smaller, or the like, than the thickness 158 to create the sealing effect noted above.

The second section 112 includes an outer surface 128 defining an outer diameter of the second section 112. In some embodiments, the outer diameter of the second section 112 can be dimensioned greater than the outermost point 130 of the first section 110. In some embodiments, the outer diameter of the second section 112 can be dimensioned substantially equal to the outermost point 130 of the first section 110. In some embodiments, as shown in FIG. 4, the outer diameter of the second section 112 can be dimensioned greater than the outermost point 130 of the first section 110. The greater outer diameter of the second section 112 can result in a higher inner pressure seal during use of the seal apparatus 100. The second section 112 includes a radial groove 132 (e.g., a relief area) formed in the inner wall 126 and extending from the inner wall 126 towards the distal end 108 of the seal apparatus 100. The radial groove 132 extends only a partial thickness of the second section 112. In some embodiments, the radial groove 132 can provide for an increased spring pressure between inner walls 118, 126, resulting in a proper seal on different types of surfaces (e.g., level or parallel surfaces, slightly non-parallel surfaces, wavy surfaces, or the like).

Figure 3:
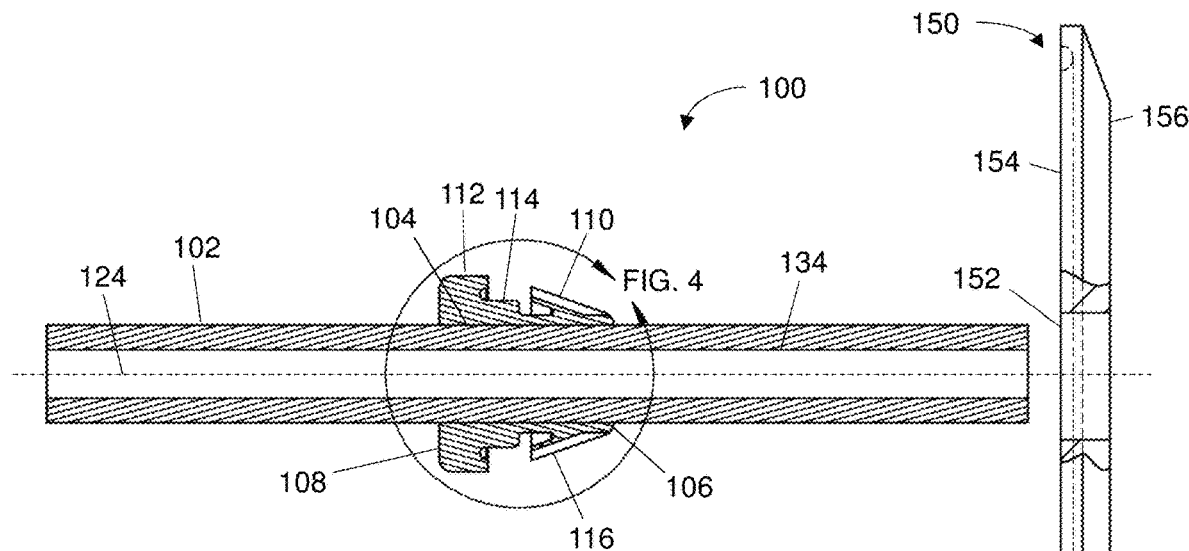
FIG. 3 is a diagrammatic, cross-sectional view of a seal apparatus and cap of FIG. 2.

As illustrated in FIG. 3, the outer diameters of the first, second and intermediate sections 110, 112, 114 are each dimensioned greater than the diameter of the opening 152 of the cap 150. During assembly, the conduit 102 can be extended through the opening 152 such that the first section 110 abuts the edges of the opening 152. Applying tension to pull the seal apparatus 100 through the opening 152 results in flexing and/or collapsing of one or more areas of the first section 110 such that the first section 110 passes through the opening 152. Particularly, either the feed side or the exit side pieces of the conduit 102 tubing are passed up through the opening on a bottom side 154 (e.g., interior or wall-facing side) of a cap 150 and then pulled through the opening 152 in the cap 150. This action causes the cone-shaped top to collapse inwards while traversing the opening 152. The flexing or collapsing is allowed by the relief areas 110 incorporated into the seal apparatus 100 design that provide the cone-shaped design space into which to compress.

After the cone-shaped top (e.g., first section 110) clears the exterior or opposing surface 156 of the cap 150, the first section 110 springs or re-expands back to its original shape (e.g., the shape shown in FIG. 1). The expanded configuration of the first section 110 forms a seal between the inner wall 118 and the surface 156 of the cap 150. At the same time, the second section 112 of the seal apparatus 100 is pulled towards the surface 154 of the cap 150 to create a seal on the opposing side of the opening 152 between the inner wall 126 and the surface 154. An additional seal is created on the interior surfaces of the opening 152 by the slightly compressed oversized walls of the seal apparatus 100 compared to the opening 152 diameter in the cap 150. Particularly, the distal portion 122 of the intermediate section 114 compresses against the inner walls of the opening 152 to form an interior seal within the opening 152. The three seals formed by the seal apparatus 100 ensure an air and fluid-tight seal between the seal apparatus 100 and the cap 150.

Figure 5:
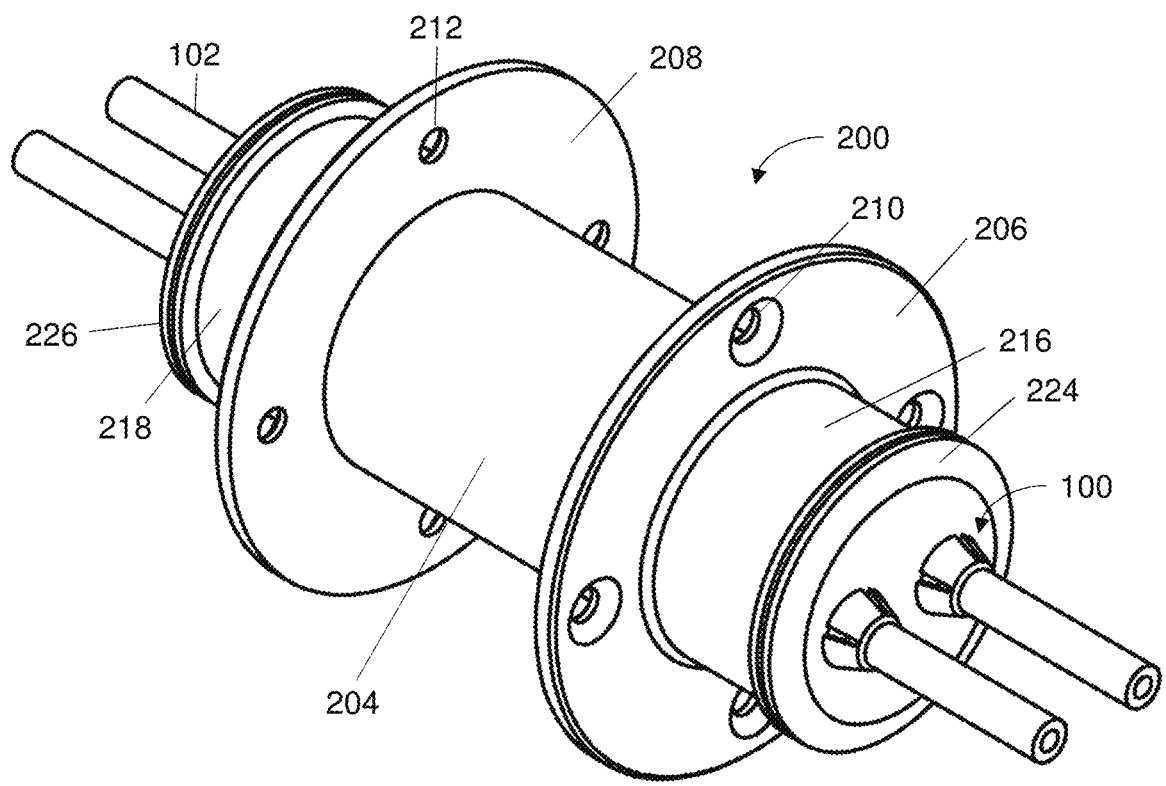
FIG. 5 is a diagrammatic, perspective view of a seal apparatus assembled with an intermediate wall apparatus used in a clean room environment in an exemplary embodiment.
Figure 6:
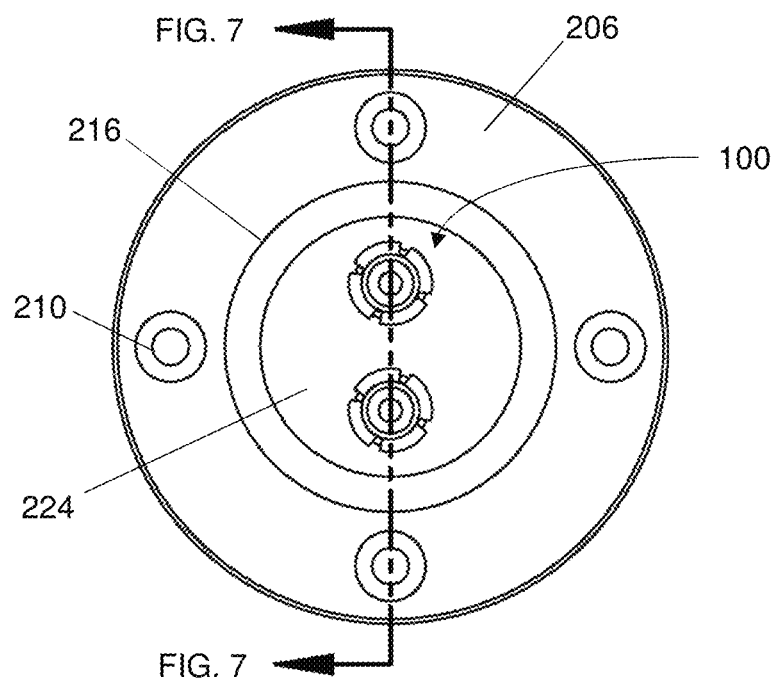
FIG. 6 is a diagrammatic, front view of a seal apparatus assembled with an intermediate wall apparatus of FIG. 5.
Figure 7:
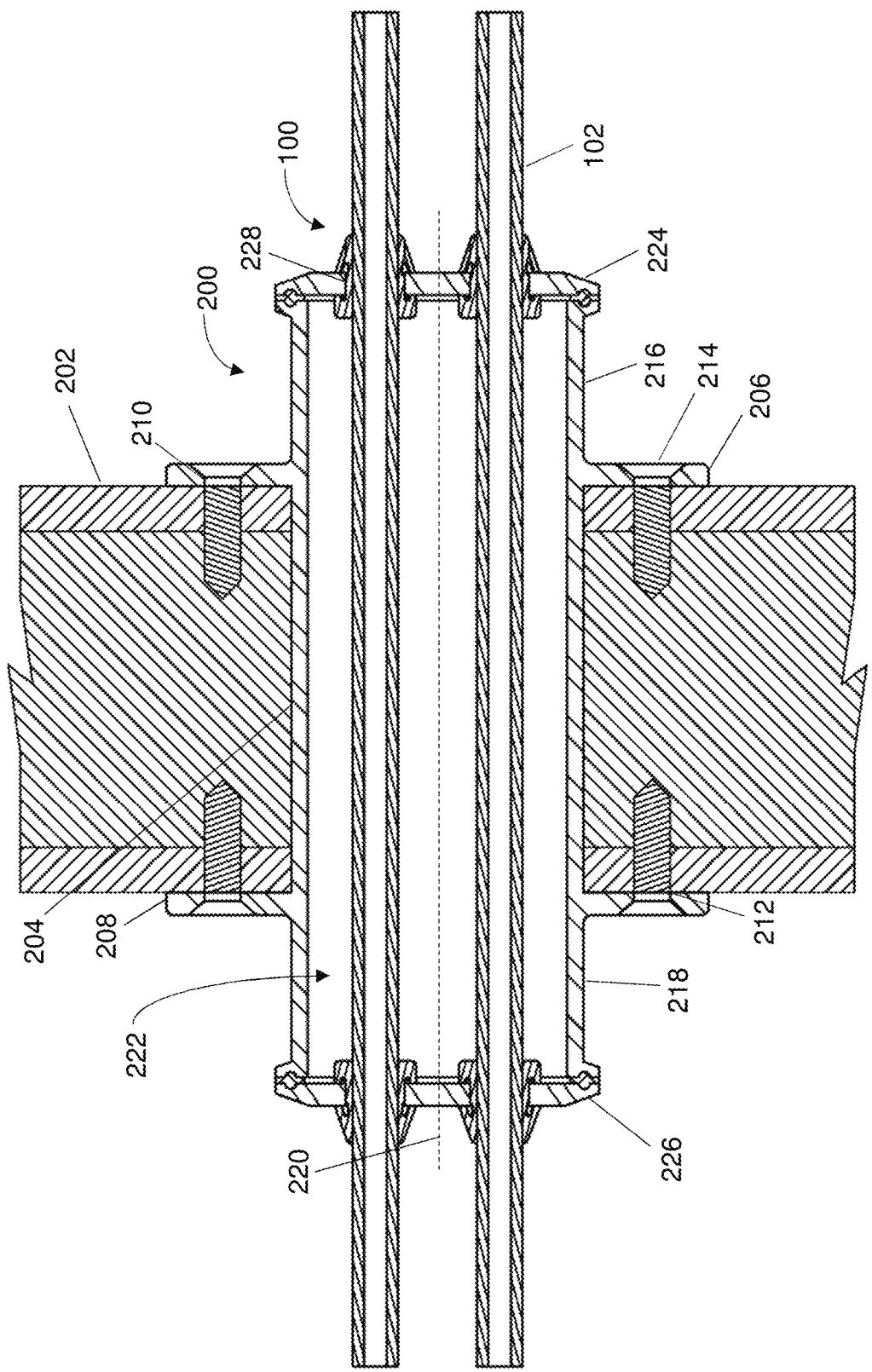
FIG. 7 is a diagrammatic, cross-sectional view of a seal apparatus assembled with an intermediate wall apparatus of FIG. 5 and installed in a clean room environment.
Figure 8:
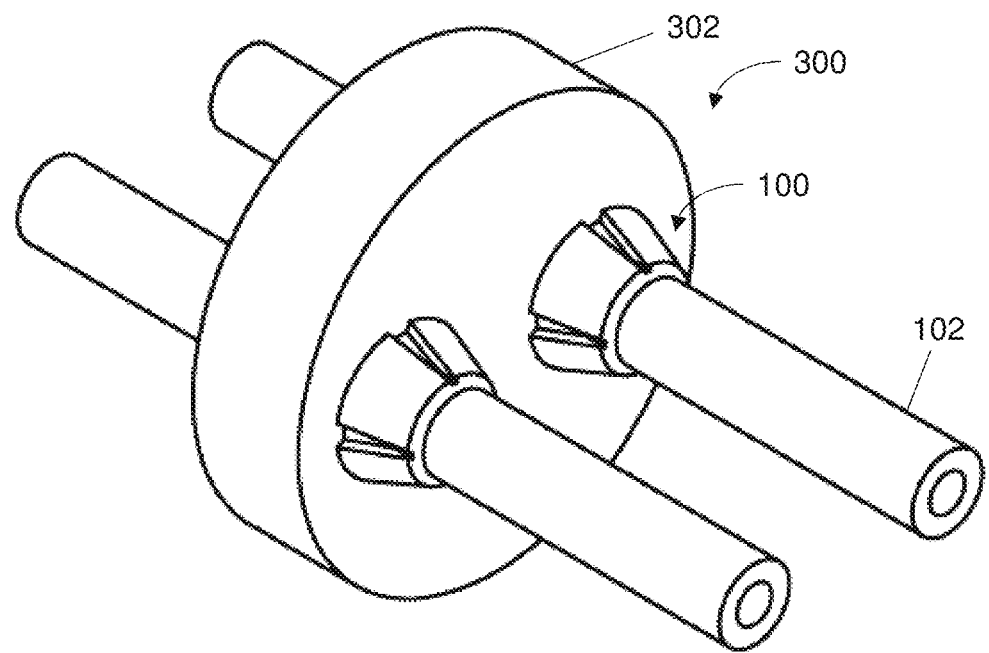
FIG. 8 is a diagrammatic, front perspective view of a seal apparatus used in conjunction with a removable cap in an exemplary embodiment.
Figure 9:
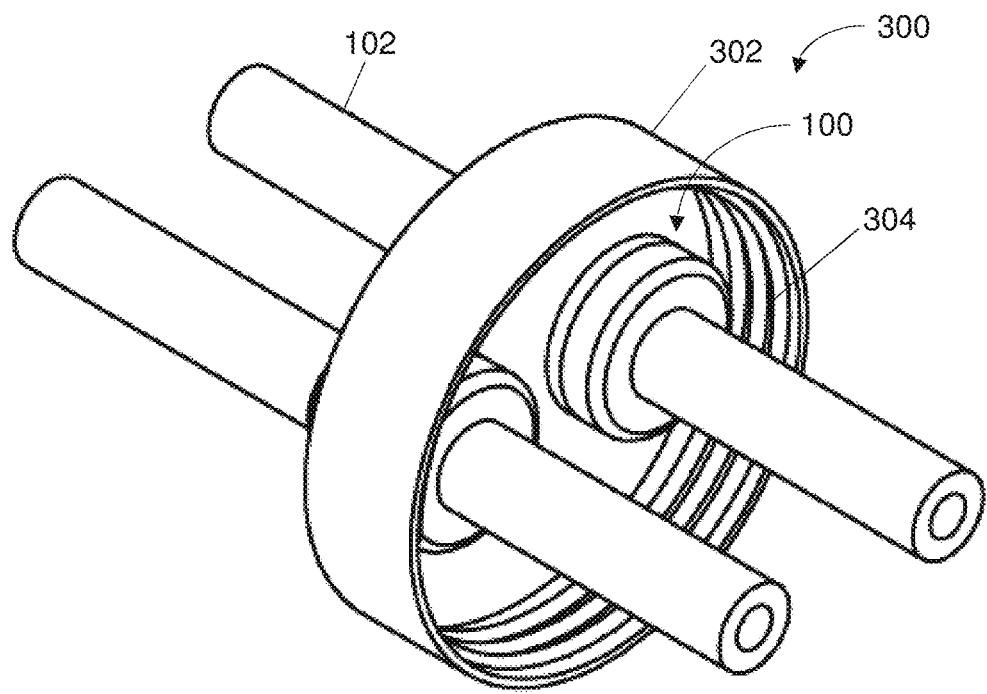
FIG. 9 is a diagrammatic, rear perspective view of a seal apparatus and removable cap of FIG. 8.
Figure 10:
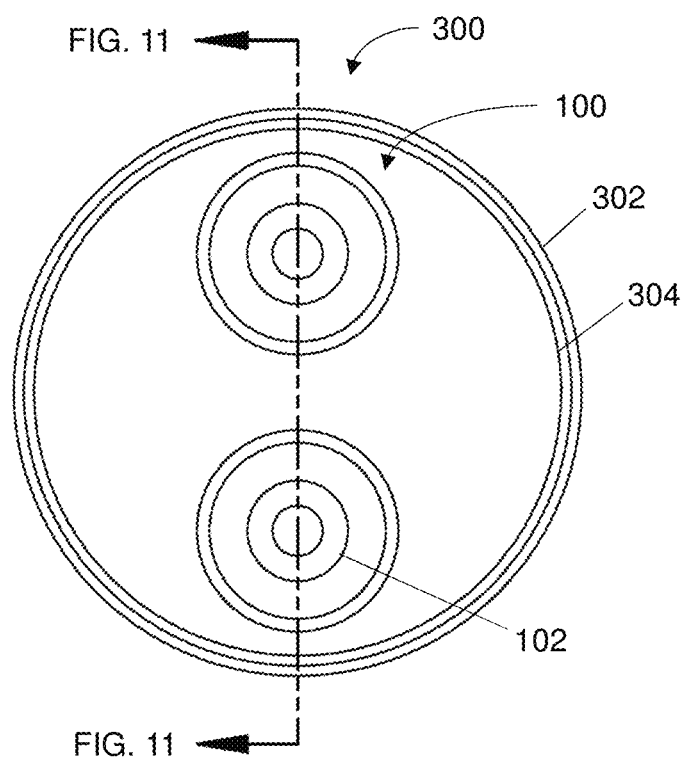
FIG. 10 is a diagrammatic, rear view of a seal apparatus and removable cap of FIG. 8.
Figure 11:
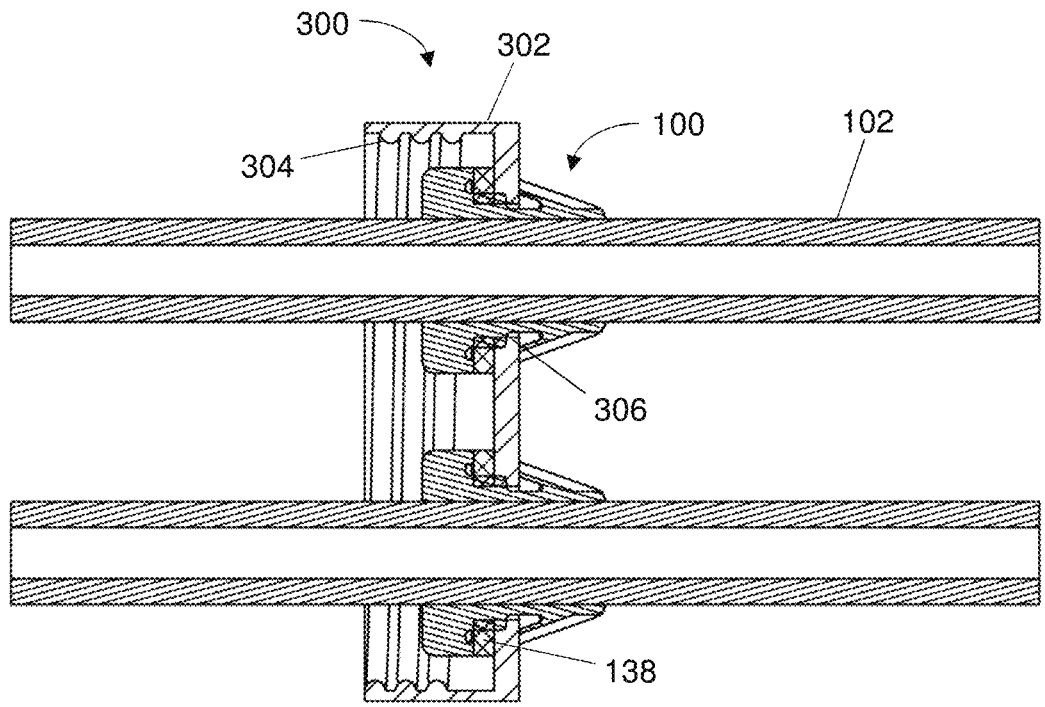
FIG. 11 is a diagrammatic, cross-sectional view of a seal apparatus and removable cap of FIG. 8.

FIGS. 5-7 are diagrammatic perspective, front and cross-sectional views of a seal apparatus 100 assembled with an intermediate wall apparatus 200 (e.g., a pass through device) for use in a clean room environment in an exemplary embodiment. It should be understood that the seal apparatus 100 of FIGS. 5-7 is similar in structure and function to the seal apparatus of FIGS. 1-4. Therefore, reference numbers are excluded for clarity of operation. Rather than having a single seal apparatus 100 on each conduit 102, as shown in FIGS. 5-7, each conduit 102 can include two seal apparatuses 100 facing in opposing directions to create a seal on opposing sides of a wall 202.

In a clean room environment, it is essential to limit any outside contaminants from being introduced. Accordingly, in one embodiment, the seal apparatus 100 can be used to form a seal on both sides of a wall 202 in the clean room when assembled with an intermediate wall apparatus 200. The intermediate wall apparatus 200 includes a central housing 204 with two mounting flanges 206, 208 extending from the central housing 204 on opposing sides and in a spaced relationship. Each flange 206, 208 includes holes 210, 212 for securing the flanges 206, 208 to opposing sides of the wall 202 with fasteners 214. The intermediate wall apparatus 200 includes cylindrical extensions 216, 218 extending front the flanges 206, 208 along the central longitudinal axis 220.

The interior of the central housing 204 and the extensions 216, 218 are connected to form an inner passage 222 through which one or more portions of the seal apparatus 100 can extend. Endpoint caps 224, 226 are secured to respective ends of the extensions 216, 218 to seal the inner passage 222. The intermediate wall apparatus 200 includes openings 228 in the caps 224, 226 for assembly with the seal apparatus 100. Although two openings 228 are shown (e.g., for an inlet and outlet conduit 102), it should be understood that any number of openings 228 can be used depending on the number of seal apparatus 100 passing through the intermediate wall apparatus 200.

The seal apparatus 100 can be assembled with the intermediate wall apparatus 200 prior to securing one or both endpoint caps 224, 226 to the extensions 216, 218. Similar to the assembly of the seal apparatus 100 with a cap 150 or lid, tubing or conduit 102 to which the seal apparatus 100 has been attached is fed through the opening 228 in the respective cap 224, 226. The top cone-like portion (e.g., the first section 110) of the seal apparatus 100 compresses initially and springs back into shape on the outer side of the cap 224, 226 to create a first seal. Due to the dimensional difference between the length 136 of the intermediate section 114 and the width of the cap 224, 226, and/or the dimensional difference between the diameter of the intermediate section 114 and the diameter of the opening 228, additional seals are created around the cap 224, 226. The bottom portion (e.g., the second section 112) seals the opposing or inner side of the opening 228, and the compressibility of the seal apparatus 100 seals the sides of the opening 228 as well. The intermediate section 114 compresses and creates a seal within the opening 228.

After the seal apparatus 100 on one end of the conduit 102 has been assembled with one cap (e.g., cap 224), the opposing seal apparatus 100 on the same conduit 102 can be assembled with the opposing cap (e.g., cap 226). In some embodiments, the conduit 102 can be flexible enough to allow for assembly of the seal apparatuses 100 on opposing sides of the intermediate wall apparatus 200 without additional slack in the conduit 102. In some embodiments, slack in the conduit 102 can be left within the passage 222 for easier installation. In such embodiments, it should be understood that the slack does not affect the fluid flow within the conduit 102. As depicted in FIGS. 5-7, the openings into the clean room can be sealed using openings in the intermediate wall apparatus 200 that is inserted or integrated with the wall 202 of the clean room. In some embodiments, openings can be formed directly in the wall 202 for assembly with the seal apparatus 100 without use of the intermediate wall apparatus 200.

FIGS. 8-11 are diagrammatic, perspective, rear and cross-sectional views of a seal apparatus 100 used in conjunction with a removable cap 300 in an exemplary embodiment. As noted above, the seal apparatus 100 can be used with removable/caps and lids. The cap 300 includes a body 302 defining an exterior surface, and threads 304 on an interior surface for mating the cap 300 with threads of a container (not shown). The cap 300 includes openings 306 extending therethrough and configured to receive the seal apparatus 100 during assembly. The number of openings 306 can depend on the application of use.

Assembly of the seal apparatus 100 with the cap 300 can be substantially similar to the assembly discussed above. In one embodiment, the seal provided by the cone-like portion of the seal apparatus 100 on top of the cap 300 can be supplemented with a sealing element 138 (e.g., silicone, a washer, combinations thereof, or the like) for caps 300 having a thinner thickness, thereby increasing the sealing effect.

Figure 12A:
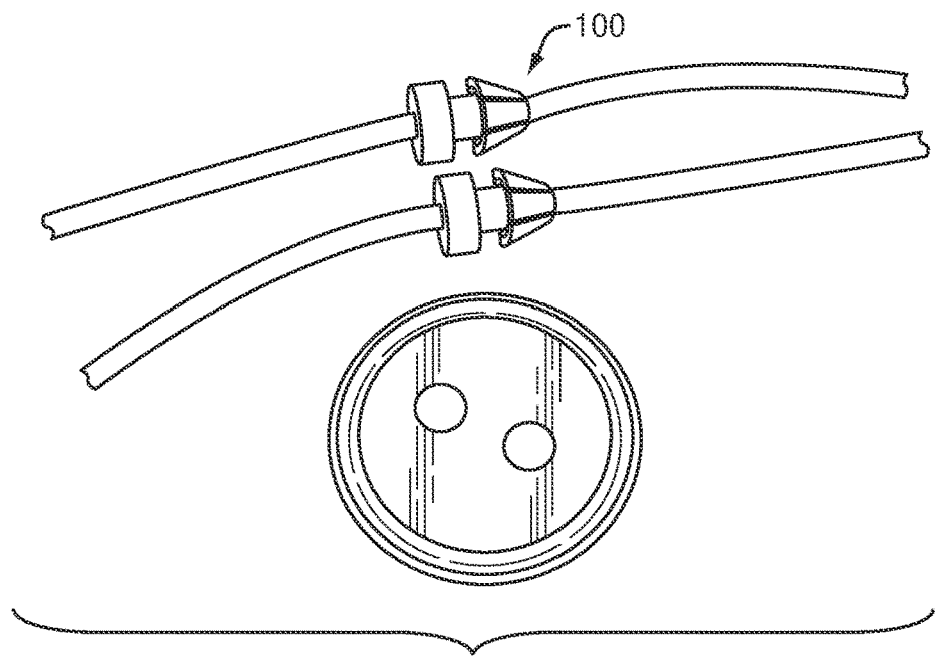
FIGS. 12A-12E depict views of the insertion and placement of a seal apparatus in conjunction with flexible fluid conduits in an exemplary embodiment.
Figure 12B:
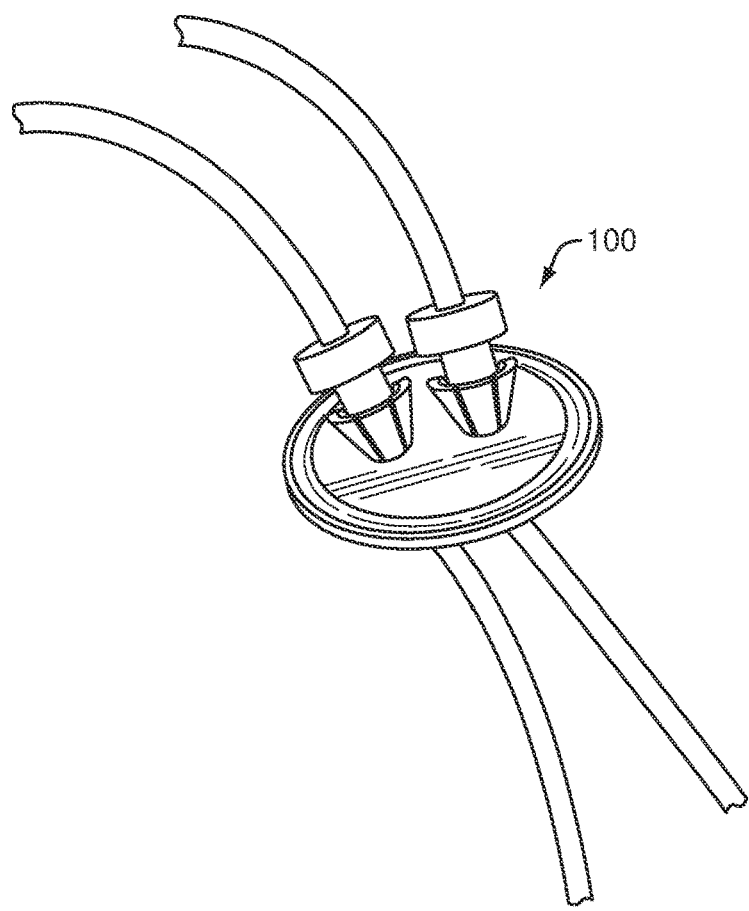
Figure 12C:
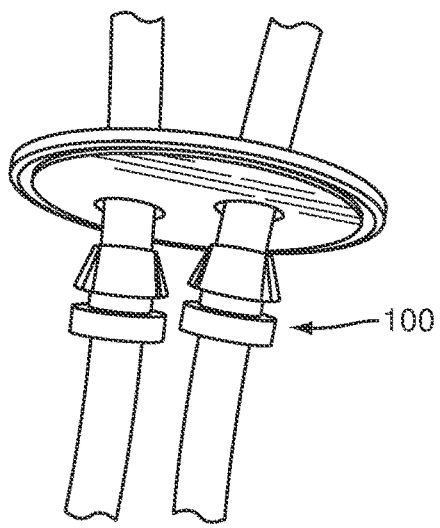
Figure 12D:
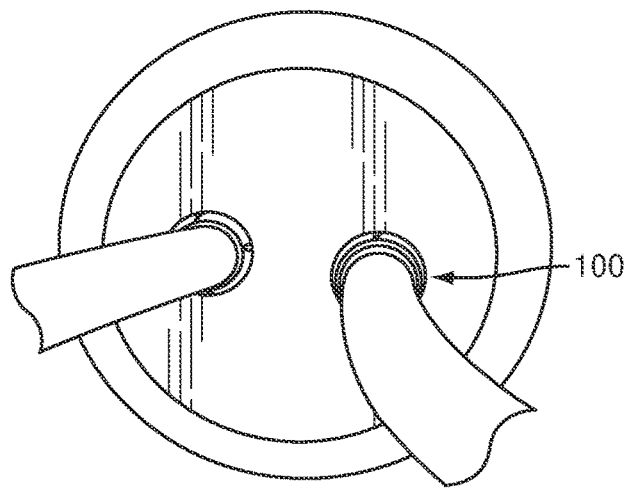
Figure 12E:
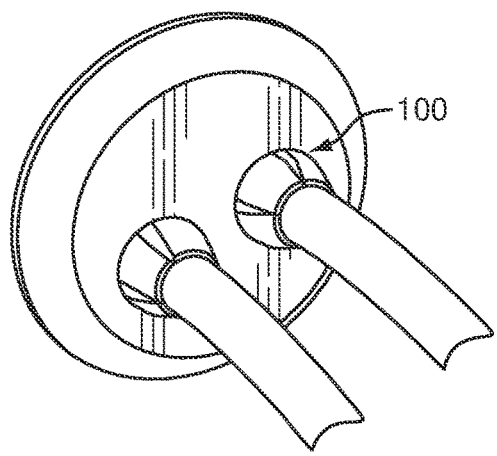

FIGS. 12A-E depict views of the insertion and placement of a seal apparatus 100 in conjunction with flexible fluid conduits in an exemplary embodiment. FIG. 12A shows a view of the seal apparatus 100 affixed to flexible conduits and a lid with openings. FIGS. 12B-C show views of the seal apparatus 100 prior to being pulled through the openings in the lid. FIG. 12D shows a view from the top of the lid and the seal apparatus 100 during the process of the top cone-like portion being pulled though the opening. As noted above, the cone-like portion of each seal apparatus 100 is compressed as the seal apparatus 100 is gradually pulled through the respective opening, and snaps outwardly after passing through the opening to create a seal on the outer surface of the lid. FIG. 12E provides a view of the seal apparatus 100 after being pulled through the opening in the lid and shows the seal formed on the top of the lid by the cone portion after re-expansion.

Figure 13A:
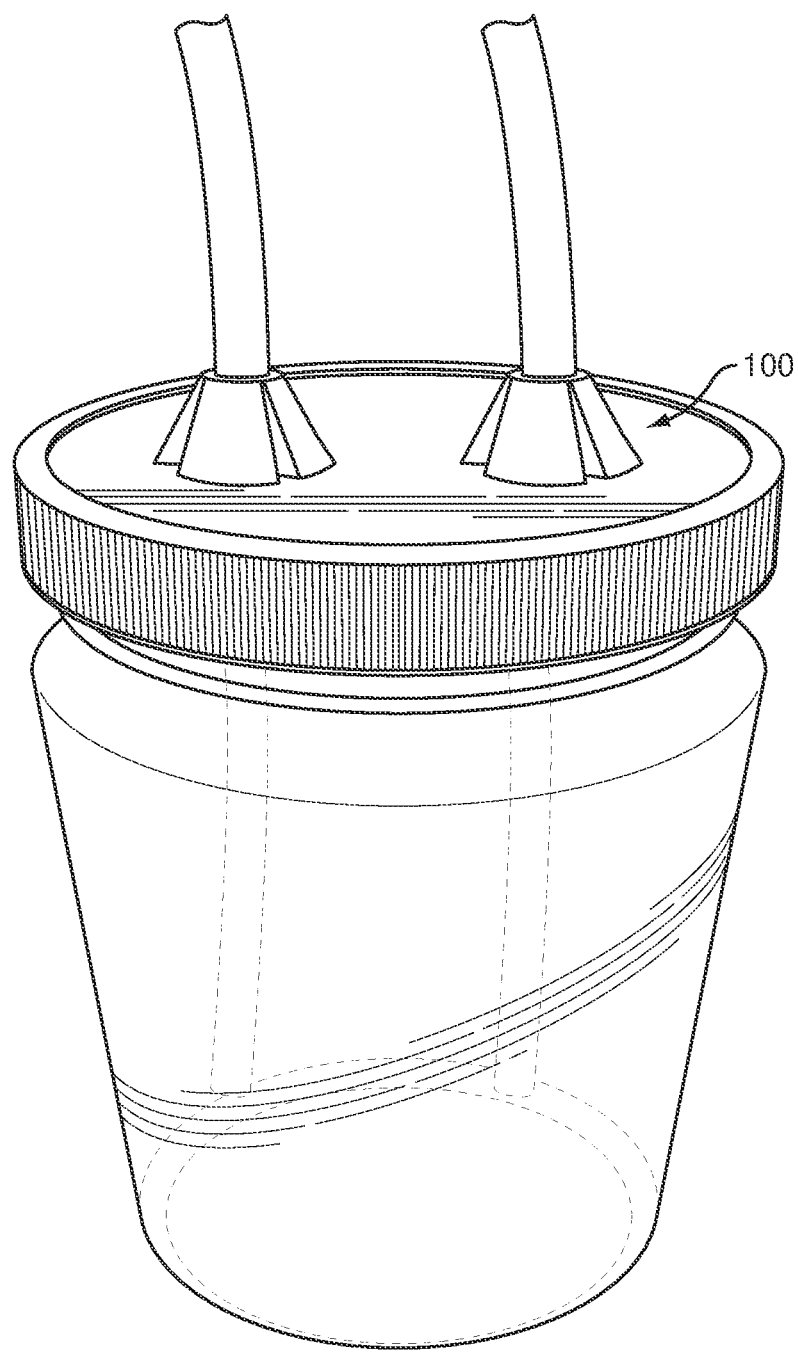
FIGS. 13A-13B depict views of the use of a seal apparatus in conjunction with a removable cap in an exemplary embodiment.
Figure 13B:
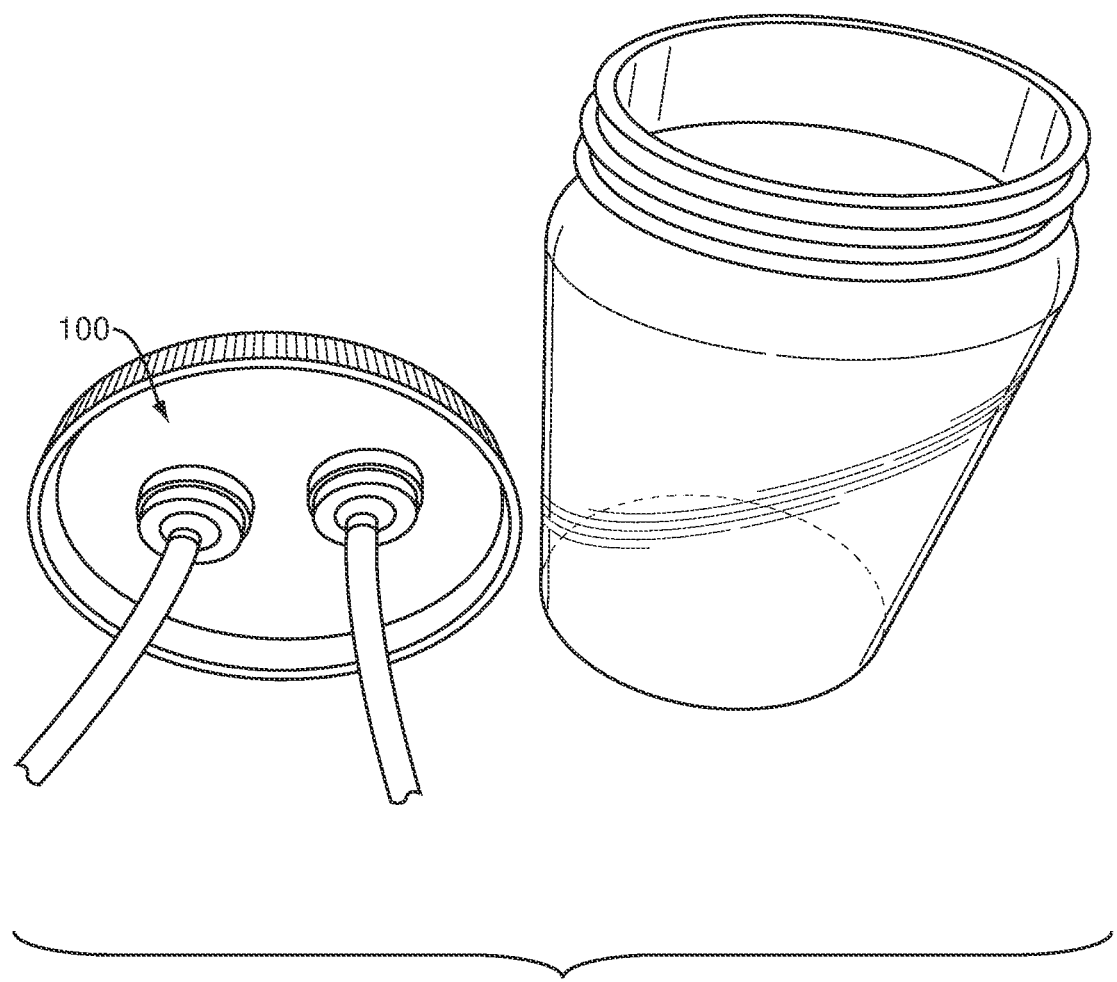

FIGS. 13A-B depict views of the use of a seal apparatus 100 in conjunction with a removable cap in an exemplary embodiment. FIG. 13A shows a view of the seal formed by the cone-like portion formed on top of the cap, while FIG. 13B shows a view of the seal formed on the bottom of the cap by the bottom portion of the seal apparatus 100.

Figure 14:
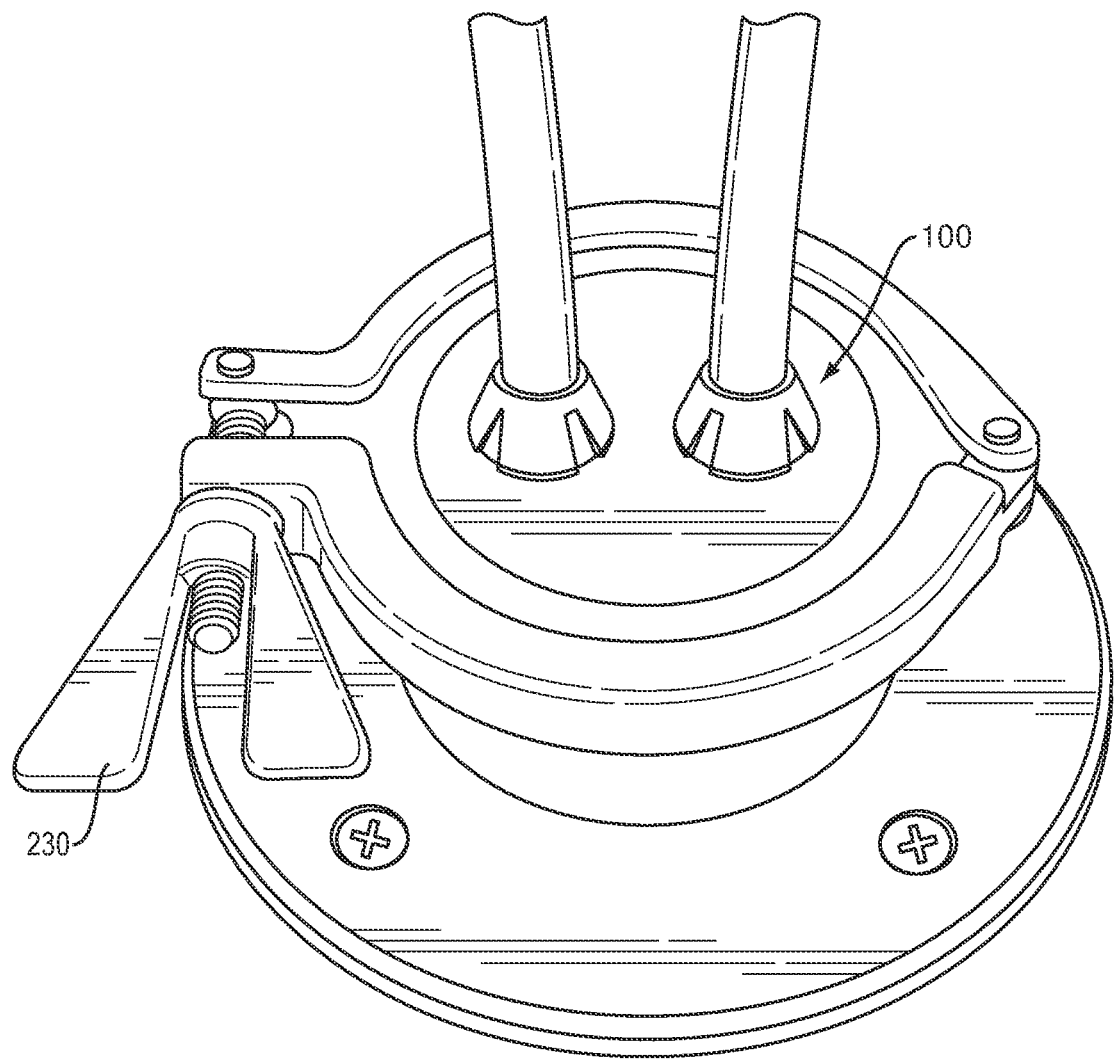
FIG. 14 depicts a view of the use of a seal apparatus in conjunction with an intermediate wall apparatus for a clean room environment in an exemplary embodiment.

FIG. 14 depicts the use of a seal apparatus 100 in conjunction with an intermediate wall apparatus for a clean room environment in an exemplary embodiment. The intermediate wall apparatus can be substantially similar to the intermediate wall apparatus 200 of FIGS. 5-7. A clamp mechanism 230 can be used to secure the endpoint cap to the extension after assembly of the seal apparatus 100 with the intermediate wall apparatus.

Figure 15:
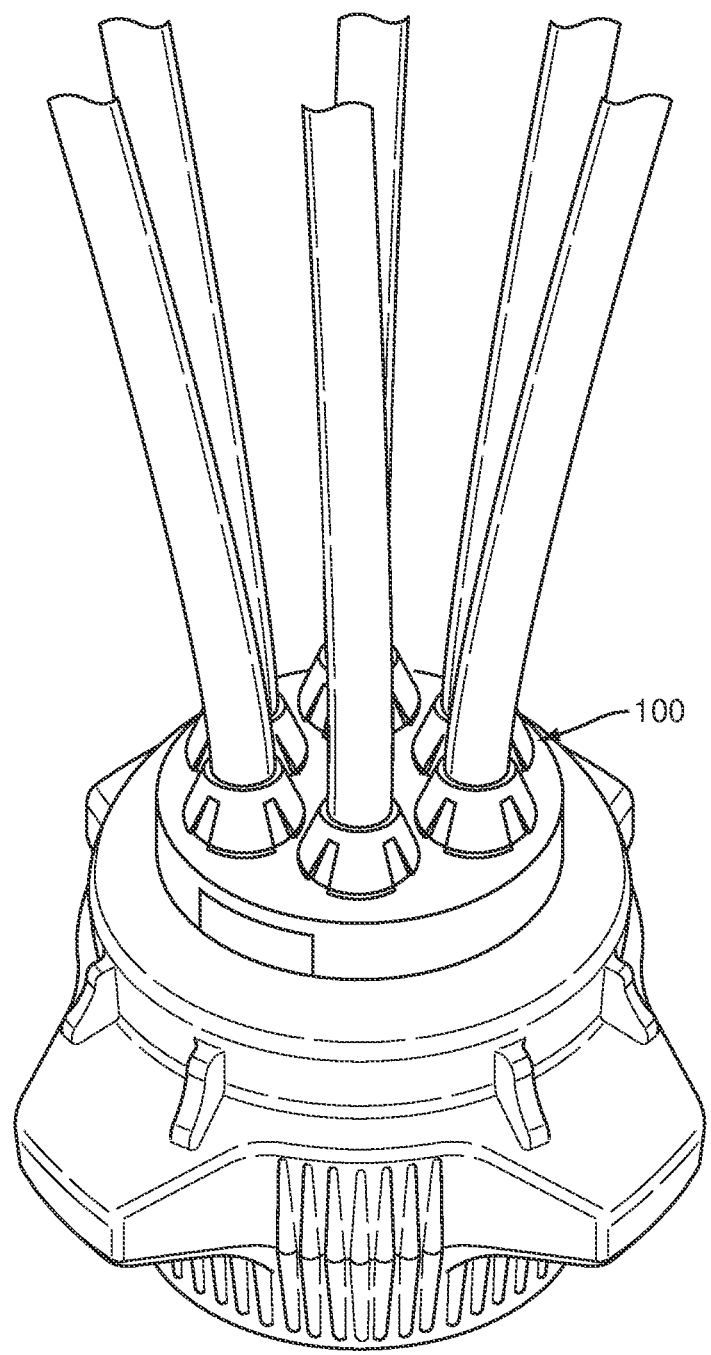
FIG. 15 depicts a view of the use of a seal apparatus in conjunction with a removable cap in an exemplary embodiment.

FIG. 15 depicts the use of a seal apparatus 100 in conjunction with a removable cap in an exemplary embodiment. Specifically, six seal apparatuses 100 are used with separate conduits and passed through individual holes in the cap during assembly. The compact configuration of the seal apparatus 100 provides the advantage of positioning multiple conduits adjacent to each other in a small surface area of the cap. Traditional sealing apparatuses include multiple components that project from the conduit and generally necessitate more surrounding area for assembly, resulting in a smaller number of seal apparatuses that can be assembled with a small cap. The exemplary seal apparatus 100 provides an efficient and compact assembly with multiple conduits positioned adjacent to each other.

Figure 16:
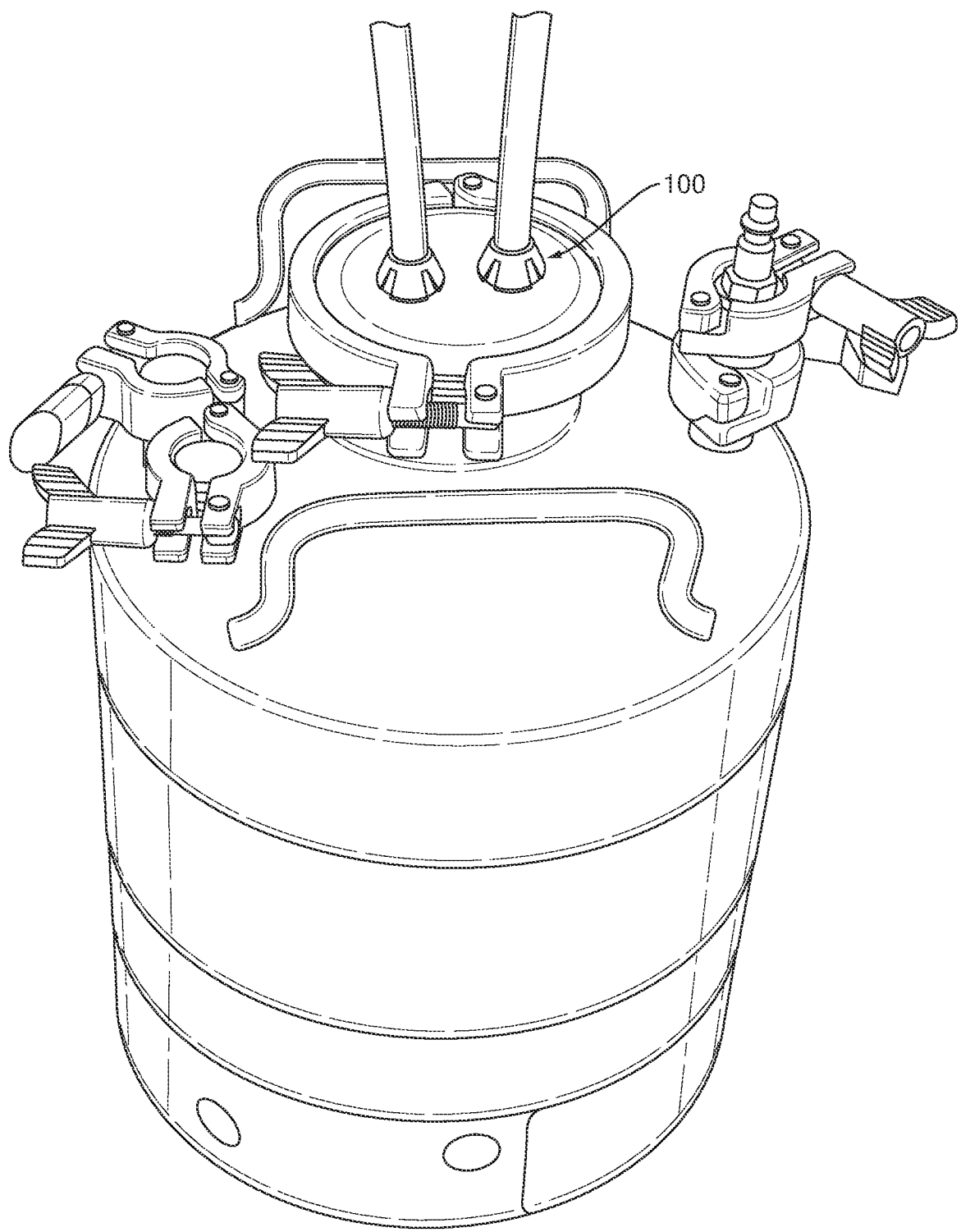
FIG. 16 depicts a view of the use of a seal apparatus in conjunction with a lid of a container in an exemplary embodiment.

FIG. 16 depicts the use of a seal apparatus 100 in conjunction with a lid of a container in an exemplary embodiment. Although two seal apparatuses 100 are shown, it should be understood that any number of seal apparatuses 100 can be used depending on the intended use of the container.

Figure 17:
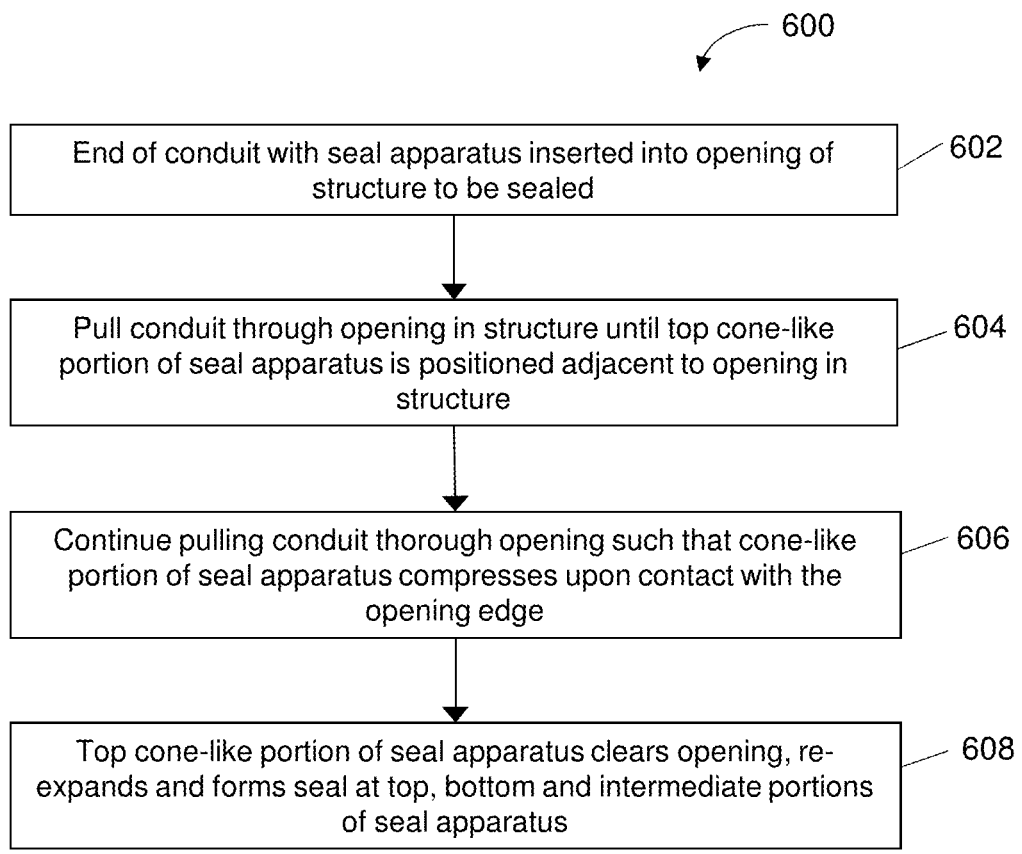
FIG. 17 is a flowchart of an exemplary sequence of steps performed in an exemplary embodiment.

FIG. 17 is a flowchart of an exemplary sequence of steps or process 600 performed in an exemplary embodiment to seal a structure (e.g., cover, lid, cap, or the like) with a seal apparatus 100. To begin, at step 602, the end of a flexible conduit that includes the seal apparatus is inserted into an opening in the structure. At step 604, the flexible conduit is pulled through the opening in the structure until the narrow portion of the top cone-like portion of the seal apparatus is adjacent to the opening. At step 606, the flexible conduit is pulled further through the opening in the structure such that the cone-like portion of the seal apparatus compresses upon contact with the opening edge. At step 608, the flexible conduit is pulled through the opening until the cone-like portion of the seal apparatus clears the opening and re-expands on the opposing side, forming a seal with the structure. Based on the configuration of the seal apparatus, seals are formed at the top, bottom and intermediate portions of the seal apparatus. Specifically, a seal is formed around the entire circumference at the wall surrounding the opening on one side with the top portion of the seal apparatus, a seal is simultaneously formed against the opposing wall with the bottom portion of the seal apparatus due to the compression of the top and bottom portions, and a seal is simultaneously formed at the interior surfaces of the opening with the intermediate portion of the seal apparatus. The seal apparatus thereby provides three separate points of sealing for the opening, ensuring an air and fluid-tight seal.

In one embodiment, the components of the seal apparatus may be produced as sterile components in a validated injection molding clean room environment, and properly bagged and sealed before exiting the room. Afterwards the seal apparatus can be autoclaved or gamma irradiated to achieve a full sterile status. In one embodiment, the components of the seal apparatus may be produced in a non-sterile environment for use in non-sterile industries, e.g., automotive, aerospace, electrical, plumbing, or the like.

Since certain changes may be made without departing from the scope of the present invention, it is intended that all matter contained in the above description or shown in the accompanying drawings be interpreted as illustrative and not in a literal sense. Practitioners of the art will realize that the sequence of steps and architectures depicted in the figures may be altered without departing from the scope of the present invention and that the illustrations contained herein are singular examples of a multitude of possible depictions of the present invention.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A seal apparatus for sealing an opening of a structure having a thickness at the opening, the seal apparatus comprising:

a first section disposed at a proximal end, the first section defining a cone-like configuration;

a second section disposed at a distal end; and an intermediate section extending between an inner wall of the first section and an inner wall of the second section to define a continuous opening extending through the first section, the second section, and the intermediate section, the continuous opening configured to receive a conduit therethrough, and the intermediate section including a first portion and a second portion with different outer diameters that form a radial step in the intermediate section;

the first section, the second section, and the intermediate section are formed as a single piece; and the first section, the second section, and the intermediate section form a plurality of fluid-tight seals between the seal apparatus and the opening of the structure.

2. The seal apparatus of claim 1, wherein the conduit is a flexible conduit.

3. The seal apparatus of claim 1, comprising a plurality of relief areas formed in the first section.

4. The seal apparatus of claim 3, wherein the relief areas extend a partial distance into a thickness of the first section and enable the first section to compress or collapse under pressure during passage of the first portion through the opening of the structure.

5. The seal apparatus of claim 1, wherein a diameter of the first section is dimensioned greater than a diameter of the opening of the structure.

6. The seal apparatus of claim 5, wherein the first section is configured to be temporarily compressed during passage through the opening of the structure, and configured to expand to an original expanded configuration after passage through the opening of the structure.

7. The seal apparatus of claim 6, wherein the inner wall of the first section forms a first of the plurality of fluid tight seals, the first fluid tight seal located between the first section and the structure after expansion of the first section to the original expanded configuration.

8. The seal apparatus of claim 1, wherein a diameter of the intermediate section is dimensioned greater than a diameter of the opening of the structure.

9. The seal apparatus of claim 8, wherein during assembly of the seal apparatus with the structure, the intermediate section is compressed within the opening of the structure to create a second of the plurality of fluid tight seals, the second fluid tight seal located between the intermediate section and the opening of the structure.

10. The seal apparatus of claim 1, wherein a length of the intermediate section is dimensioned smaller than the thickness of the structure at the opening.

11. The seal apparatus of claim 10, wherein during assembly of the seal apparatus with the structure, the inner wall of the first section and the inner wall of the second section are configured to be compressed against opposing surfaces of the structure due to the dimensional difference between the length of the intermediate section and the thickness of the structure at the opening.

12. The seal apparatus of claim 1, wherein a third of the plurality of fluid tight seals is located between the intermediate section and an inner surface of the opening of the structure.

13. The seal apparatus of claim 1, comprising a relief groove formed in an inner wall of the second section.

14. The seal apparatus of claim 1, wherein the continuous opening extending through the first section, the second section, and the intermediate section defines a uniform inner diameter.

15. The seal apparatus of claim 1, wherein the intermediate section extends between inner walls of the first and second sections.

16. A system for sealing an opening of a structure having a thickness at the opening, and a first side and a second side on opposing sides of the opening, the system comprising:
   a first seal apparatus, comprising:
      a first section disposed at a proximal end, the first section defining a cone-like configuration;
      a second section disposed at a distal end;
      an intermediate section extending between inner walls of the first and second sections to define a continuous opening extending through the first section, the second section, and the intermediate section, the intermediate section including a first portion and a second portion with different outer diameters that form a radial step in the intermediate section; and
   a conduit disposed within and extending through the continuous opening of the first seal apparatus;
   the first section, the second section, and the intermediate section are formed as a single piece; and
   a connection between the first seal apparatus and the opening of the structure forms a plurality of fluid-tight seals.

17. The system of claim 16, wherein:
the first seal apparatus is bonded to the conduit; or a position of the first seal apparatus along the conduit is maintained via a friction fit.

18. The system of claim 16, wherein a connection formed between the first seal apparatus and the conduit is a sterile seal.

19. A method of sealing an opening of a structure having a thickness at the opening, the method comprising:
   positioning a first section of a seal apparatus adjacent to the opening of the structure, the seal apparatus including: (i) the first section disposed at a proximal end and defining a cone-like configuration, (ii) a second section disposed at a distal end, and (iii) an intermediate section extending between the first and second sections to define a continuous opening extending through the first section, the second section, and the intermediate section, the continuous opening configured to receive a conduit therethrough, and the intermediate section including a first portion and a second portion with different outer diameters that form a radial step in the intermediate section;
   compressing the first section during passage of the first section through the opening of the structure; and
   expanding the first section into an expanded configuration after passage of the first section through the opening of the structure;
   the first section, the second section, and the intermediate section are formed as a single piece; and
   a connection between the seal apparatus and the opening of the structure forms a plurality of fluid-tight seals.

* * * * *